(12) United States Patent
Hathaway (10) Patent No.: US 11,541,247 B2
(45) Date of Patent: Jan. 3, 2023

(54) MAGNETIC STIMULATION PROBE

(71) Applicant: George D. Hathaway, King (CA)

(72) Inventor: George D. Hathaway, King (CA)

(\*) Notice: Subject to any disclaimer, the term of this patent is extended or adjusted under 35 U.S.C. 154(b) by 674 days.

(21) Appl. No.: 16/240,084

(22) Filed: Jan. 4, 2019

(65) Prior Publication Data

US 2019/0201708 A1 Jul. 4, 2019

Related U.S. Application Data

(60) Provisional application No. 62/613,541, filed on Jan. 4, 2018, provisional application No. 62/620,022, filed on Jan. 22, 2018.

(51) Int. Cl.
*A61N 2/02* (2006.01)
*A61B 5/06* (2006.01)

(52) U.S. Cl.
CPC . *A61N 2/02* (2013.01); *A61B 5/06* (2013.01)

(58) Field of Classification Search
CPC .............. A61B 5/062; A61B 5/06; A61N 2/02
See application file for complete search history.

(56) References Cited

U.S. PATENT DOCUMENTS

| 2009/0270945 A1* | 10/2009 | Markoll | A61N 2/02 607/50 |
| 2013/0317281 A1* | 11/2013 | Schneider | A61N 2/008 600/13 |
| 2014/0357935 A1* | 12/2014 | Ilmoniemi et al. | A61N 2/004 600/13 |
| 2015/0265830 A1* | 9/2015 | Simon | A61N 1/36034 600/13 |

\* cited by examiner

*Primary Examiner* — Christine H Matthews
*Assistant Examiner* — Joshua Daryl D Lannu
(74) *Attorney, Agent, or Firm* — Lorenz & Kopf, LLP (57) ABSTRACT

A magnetic stimulation probe is provided to produce a probe electromagnetic field within a patient. The magnetic stimulation probe has a first generally planar magnetic field generating coil having a first coil trace having a decreasing radial spiral which passes about a first central portion, the first coil trace having a first electric current traveling in a first direction and having a first plurality of separated portions each having a first respective set of different radii from the first central portion along a bisecting line. The first planar coil has a second coil trace having a second electric current traveling in a second direction which is parallel to the first direction, and having a second plurality of separated portions each having a second respective set of different radii from the first central portion along the bisecting line along the bisecting line. Two such coils can be arranged to produce a high intensity focused magnetic field at a distance from the probe. The probe electromagnetic field is operable to induce a current in a conductive material.

20 Claims, 5 Drawing Sheets

MAGNETIC STIMULATION PROBE

CROSS-REFERENCE TO RELATED APPLICATIONS

This application Claims priority to Provisional patent applications 62/613,541 filed Jan. 4, 2018 and 62/620,022 filed Jan. 22, 2018. The entity of these applications are herein incorporated by reference.

FIELD

The present disclosure is directed to a magnetic stimulation probe, and more particularly to an improved magnetic coil configuration to direct magnetic stimulation to a selected or planned region of an anatomy.

BACKGROUND

The statements in this section merely provide background information related to the present disclosure and may not constitute prior art.

Magnetic stimulation procedures can be performed on a patient for various purposes. Because many diagnostic, investigative, therapeutic and other procedures are performed within or affect a patient's internal anatomy, it is desirable to provide a system that provides a strong and localized magnetic field to affect the patient during a procedure. Additionally, certain procedures such as moving magnetically-tagged pharmaceuticals to a specified region of the body, or activating magnetically-tagged pharmaceuticals may be facilitated by such a magnetic field.

In the case of stimulation of a patient's internal anatomy, a principal requirement is the establishment of an internal electric field in the area of stimulation which generally results in an electric current associated therewith depending on the conductivity of the medium in which the electric field is present. The principal governing equation for such electric field generation is the Maxwell-Faraday Equation:

$$\nabla \times E = -\partial B / \partial t$$

which states that an electric field E is established due to the time rate of change of a magnetic field B. Thus the faster the magnetic field varies (rises or falls) the stronger the resulting electric field, and thus the induced current.

The time rate of change of the magnetic field produced by an electromagnetic coil is dependent on the rate of change of the electric current in the coil. The factor which prevents fast rise or fall times of the electric current in magnetic coils is the termed the inductance of the coil. The inductance of the coil is dependent on several factors including the geometric configuration of the coil windings or traces. The typical method of winding a magnetic coil well known in the art is to employ a single conductor wound in a loop or loops from one terminal to the other. This winding configuration results in a relatively large inductance in general. This relatively large inductance requires relatively increased electric current to power the coils and thus reduces power efficiency.

In 1894, N. Tesla taught (U.S. Pat. No. 512,340) that an interleaved winding configuration would greatly reduce the inductance of magnetic coils and specifically planar spiral coils which are generally used in the production of magnetic fields in a patient's internal anatomy. The interleaved winding configuration of U.S. Pat. No. 512,340 consists of two insulated conductors wound side-by-side in a flat spiral and so interconnected as to increase the inter-turn capacitance, thus reducing the effective inductance of the coil.

Magnetic stimulation procedures can be performed with the magnetic field being produced by a single coil or adjacent pairs or multiples of coils. Typical coils known in the art however, due to the time required to establish or collapse a magnetic field, have limited electric field-producing efficiency and effective distance and focality. Various coil configurations have been proposed to overcome these problems with limited success. It is desirable, therefore, to provide a more efficient coil design whose benefits include faster rise and fall times of the magnetic field, lower driving current required to power the coils, increased penetration distance and increased focality.

SUMMARY

Further areas of applicability will become apparent from the description provided herein. It should be understood that the description and specific examples are intended for purposes of illustration only and are not intended to limit the scope of the present disclosure.

According to the various embodiments, a system to provide a non-invasive procedure for affecting a patient's internal anatomy or affecting suitable pharmaceuticals within the body is disclosed. A magnetic stimulation probe is provided to produce a probe electric field within a patient. The system includes a magnetic stimulation probe operable to produce a probe magnetic field and ultimately an electromagnetic field, wherein the probe electromagnetic field is operable to induce a current in a conductive or partially conductive material such as is found in a patient's internal anatomy. The system can include a magnetic stimulation probe having a single coil, or a pair of coils, or multiple coils of conductive material in a generally planar configuration or solenoidal configuration or any other configuration and a controller operable to drive a current through the coil or coils so that the coil produces a magnetic field.

In the case of generally planar coils, a magnetic stimulation probe consisting of a single coil has a first generally planar magnetic field generating coil having a first coil trace having a decreasing radial spiral which passes about a first central portion, the first coil trace having a first electric current traveling in a first direction and having a first plurality of separated portions each having a first respective set of different radii from the first central portion along a bisecting line. The first planar coil has a second coil trace having a second electric current traveling in a second direction which is parallel to the first direction, and having a second plurality of separated portions each having a second respective set of different radii from the first central portion along the bisecting line. The first trace of the first planar coil and the second trace of the first planar coil are thus interleaved side-by-side and interconnected such that the current from the driving source of current passes first through the first trace and then through the second trace in the same direction before returning to the current source.

According to various embodiments, system to navigate a non-invasive procedure on an anatomy is disclosed. The system can include an instrument having at least a pair of coils of conductive material and a controller operable to drive a current through the coils so that the coil produces an electromagnetic field. A magnetic stimulation probe is provided to produce a probe electromagnetic field within a patient.

In the case of generally planar coils, a magnetic stimulation probe consisting of two coils has first and second generally planar magnetic field generating coils, both coils having first coil traces having a decreasing radial spiral which passes about first and second central portions, which portions can be separated one from the other. In each coil, the first coil traces have a first electric current traveling in a first direction and having a first plurality of separated portions each having a first respective set of different radii from the first central portion along a bisecting line. In each coil, the second coil traces have a second electric current traveling in a second direction which is parallel to the first direction. The second coil traces have a second plurality of separated portions each having a second respective set of different radii from the first central portion along the bisecting line.

The first coil traces of both planar coils and the second coil traces of both planar coils are thus interleaved side-by-side and connected such that the current from the driving source of current passes first through the first trace of the first planar coil and then through the second trace of the first planar coil in the same direction.

In order to produce the required focused magnetic field of high intensity at a distance from the face of the magnetic stimulation probe generally on a line perpendicular from the center of a line bisecting the first and second central portions, it is advantageous that the magnetic flux from the first magnetic field generating coil and the magnetic flux from the second magnetic field generating coil be of opposite polarity. In order to achieve this, the free ends (terminals) of the traces of the first and second coil traces in the first and second magnetic field generating coils are so interconnected as to ensure this said opposing magnetic flux polarity and provide a single current path from and to the driving source of current. Alternately, each of the magnetic field generating coils of the magnetic stimulation probe can be connected individually to single or multiple driving current sources or in other interconnections known to those skilled in the art to achieve the same desirable outcome.

In order to produce the required focused magnetic field of high intensity at a distance from the face of the magnetic stimulation probe it is also advantageous to alter the distance between the central portions of the magnetic field generating coils. Typically there is a critical separation distance between the central portions which provides both the highest magnetic field intensity at the maximum distance perpendicular to the face of the magnetic field generating coils as well as optimum focality. In some cases, the magnetic field generating coils may have all or portions of their traces overlapping.

Further, the production of the required focused magnetic field of high intensity at a distance from the face of the magnetic stimulation probe may be advantageously obtained by arranging for non-uniform side-by-side distances between the interleaved traces of the magnetic field generating coils as displaced from the central portion.

Additionally, increasing the inter-turn, or inter-winding, or inter-trace capacitance of the magnetic field generating coils will reduce the effective inductance and thus increase the power efficiency of the magnetic field generating coil. In order to take full advantage of this effect, it is advantageous to employ flat ribbon solid conductor or preferably Litz wire, or generally rectangular cross-section shaped conductors for the coil traces. In this manner the individual traces of the magnetic field generating coil can be placed arbitrarily close to one another depending on operating voltage, thus increasing the inter-turn capacitance as required. Tests with an impedance analyzer show a significant reduction in inductance by approximately 15% over traditionally wound coils.

In order to be adaptable to various portions of a patient's anatomy, it is further advantageous to alter the angle subtended by the planes of the generally planar magnetic field generating coils there by conforming to various parts of a patient's anatomy whilst optimizing the focusing and maximizing the intensity of the magnetic field so generated.

DRAWINGS

The drawings described herein are for illustration purposes only and are not intended to limit the scope of the present disclosure in any way.

FIGS. 2a and 2b are detailed views of a magnetic stimulation probe according to the present teaching. FIG. 2c is a detailed view of a magnetic stimulation probe according the present teaching using an alternate winding method to that shown in FIG. 2a;

DETAILED DESCRIPTION

The following description is merely exemplary in nature and is not intended to limit the present disclosure, application, or uses.

Figure 1:
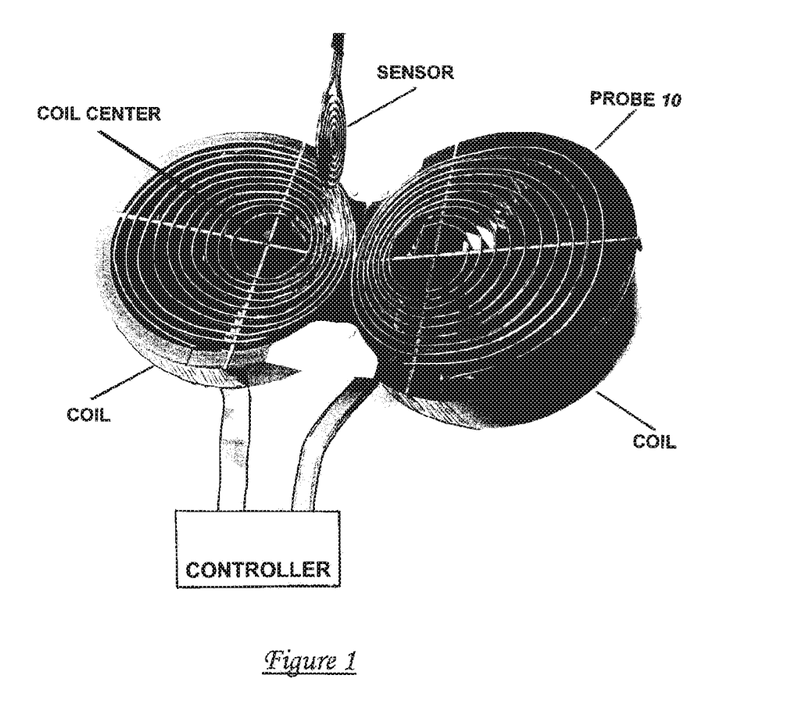
FIG. 1 is an environmental view of a magnetic stimulation probe according to the various embodiments.

FIG. 1 depicts a general view of an example magnetic stimulation probe including the probe 10, two magnetic field coils disposed one from the other about coil centers, a controller which controls the current through the coil or coils, and a sensor above the mid-line of the coils to measure the resulting magnetic field at a perpendicular distance from the face of the probe.

Figure 2A:
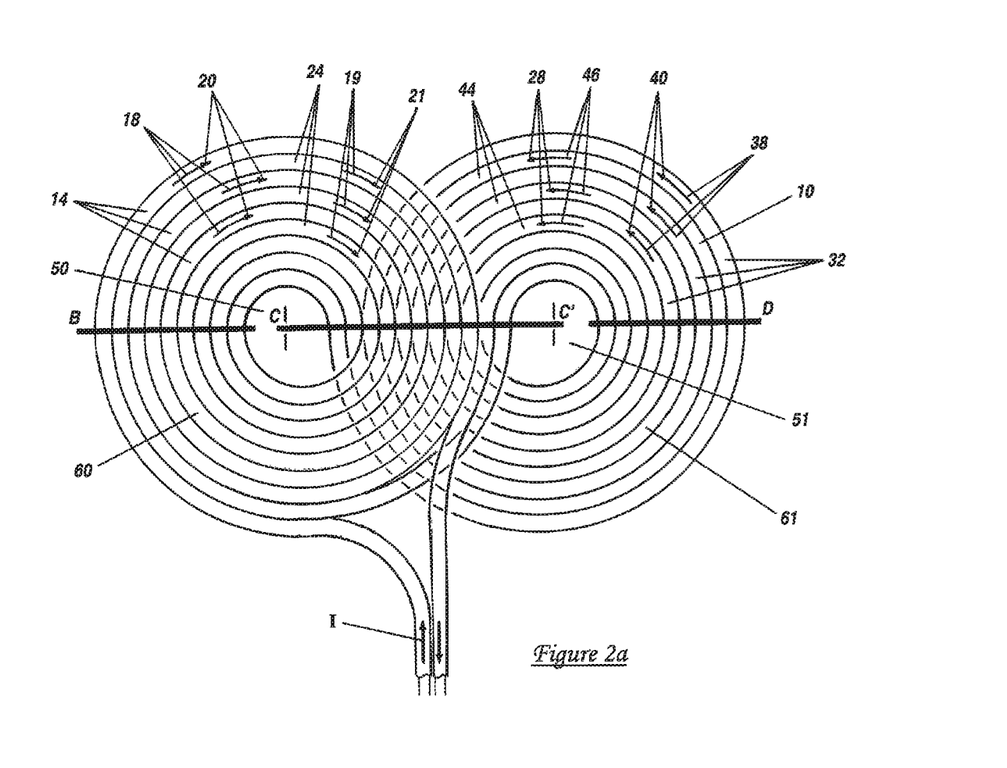
FIG. 2a is schematic representation of a magnetic stimulation probe employing substantially circular conductors.

As shown in FIG. 1 and FIG. 2a the first and second coils can have a circular exterior surface having a constant radius, and have a first centerline B-C and a second centerline C'-D. A hollow center portion of the first and second coil can similarly have a constant radius. The first and second centerlines B-C and C'-D can be displaced from each other.

The first generally planar magnetic field generating coil having a first coil trace having a decreasing radial spiral which passes about a first central portion, the first coil trace has a first electric current traveling along a first directional path and having a first plurality of separated portions each having a first respective set of different radii from the first central portion along a bisecting line. The first coil trace has a first end at a first outer surface and a second end at an inner surface of the coil. The first planar coil has a second coil trace having a second electric current traveling in a second directional path which is parallel to the first direction in adjacent segments of the first and second traces. The second plurality of separated portions each has a second respective set of different radii from the first central portion line along the bisecting line. The second trace has a third end at the first outer surface and a fourth end at an inner surface of the coil. The first and second coils and coil segments are alternated and interleaved along the bisecting line. The probe electromagnetic field is operable to induce a current in a conductive material, the first and third ends preferentially being electrically coupled.

Figure 2B:
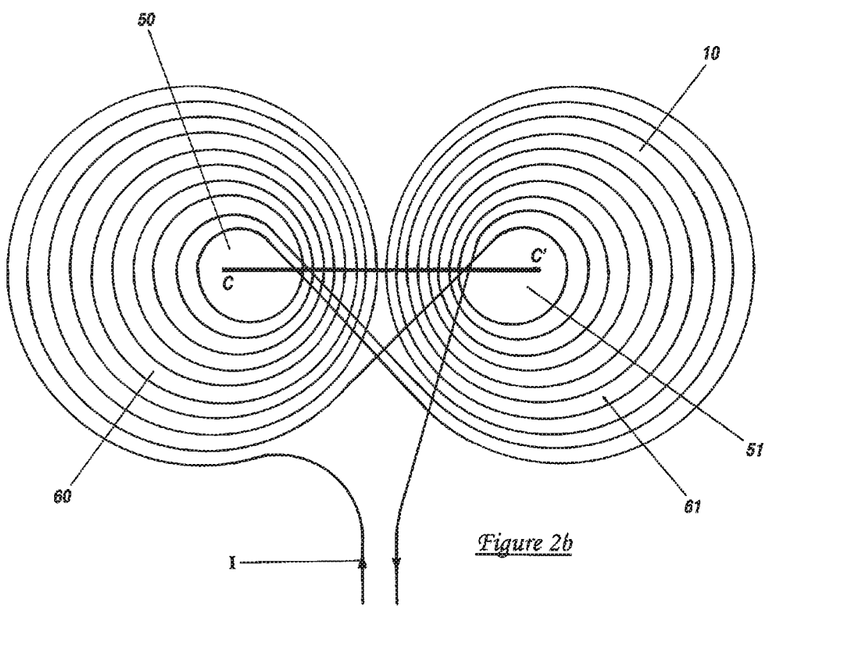
FIG. 2b is a schematic representation of the magnetic stimulation probe shown in FIG. 1 employing substantially rectangular conductors.
Figure 2C:
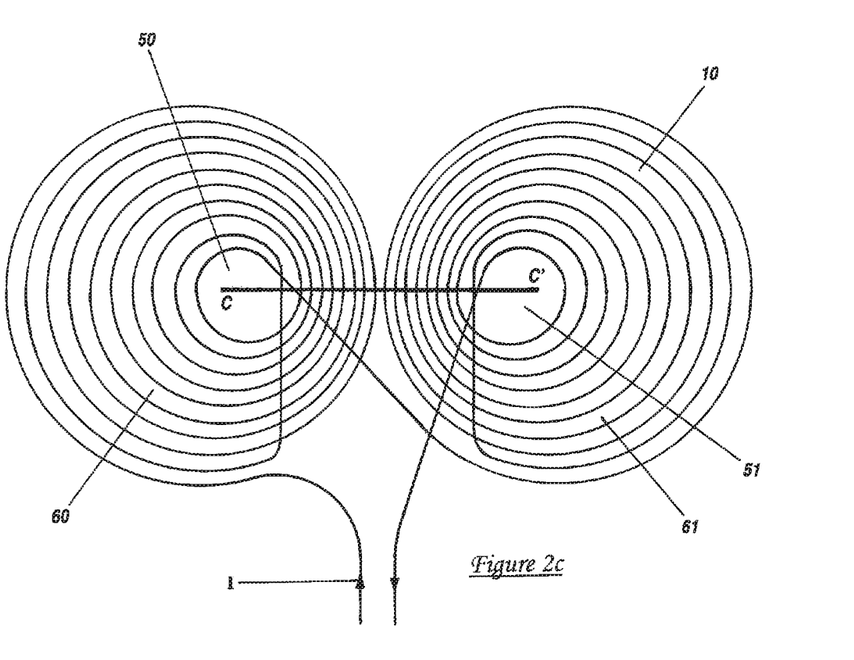

Illustrated in detail in FIGS. 2a-2c, a magnetic stimulation probe 10, such as a transcranial magnetic stimulation probe. The magnetic stimulation probe 10, as discussed further herein, includes a pair of stimulation coils 60 and 61. The stimulation coils can produce a field that is focused at a selected position in space.

Figure 3:
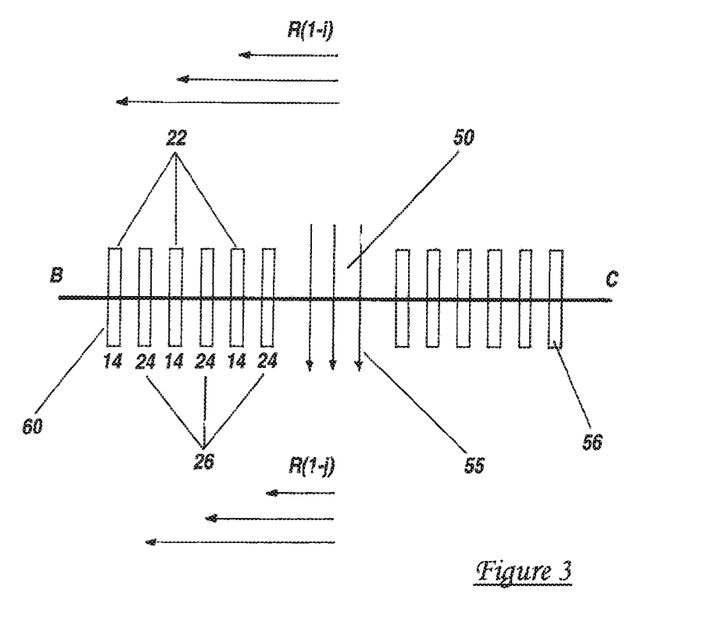
FIG. 3 represents a close-up segmented side view of trace orientation of one coil according to the present teaching.

Further, the coils 60, 61 can include selected central portions which are disposed along coil center line C and C', that is, a line bisecting the first and second central portions, 50 and 51. The centers can be provided of any appropriate size to create a selected field relative to the probe 10, and as described later, form a central portion which allows the disposition of the coil traces. Generally, a current I can be driven through the coils 60, 61 which will produce a magnetic field substantially perpendicular to the direction of the current. For example, FIG. 3 shows a disposition of substantially rectangular current conductors 56 disposed about a central portion 50 of one of a pair of magnetic field coils 60 of probe 10. A magnetic field 55 can be produced in the direction of arrows in coil 60 depending on the direction of the electrical current in the conductors. The magnetic fields, generally in the direction of arrows 55 of one coil 60 and another coil 61 can be arranged to cooperate to produce a more focused and higher intensity magnetic field along an axis where the two coils meet. In addition, a combined or cooperative field can be made to move along this axis or off-axis depending on the control of current through each coil.

The cooperative field position/direction can be substantially focused, minimally dispersed, and strong relative to the two individual fields produced by the two coils. Therefore, the area of stimulation, which is the area being affected by the cooperative field of the probe, can be substantially precise and strong. For example, the probe can form a focused stimulation region that is a distance from the center of the first coil and from the center of the second coil.

The probe 10 may have an alignment member located substantially between the central portions of coils 60 and 61 configured to allow the placement of the probe 10 adjacent a patient's body. The magnetic stimulation probe 10 is operable to stimulate a selected portion of the patient and is operable to induce a current in a conductive material. Optionally, the alignment member and the magnetic stimulation probe are formed as a single unit.

Because the position of the focused region is known relative to various portions of the probe, the focused region can be positioned relative to the patient. The navigation of the focused region can be based upon movement of the probe 10, or based on the relative strengths and direction of the currents through the coils 60 and 61 according to various embodiments.

With reference to FIG. 1, the probe 10 is generally operated with a probe driver or controller system. As discussed above, the probe 10, according to various embodiments, operates by producing or inducing an electric stimulation within a conductive material. The induction is formed by moving a current through the coils 60 and 61 of the probe 10. The two currents can be provided at different frequencies, strengths and phases as is obvious to those skilled in the art.

According to FIGS. 2a and 3, the probe 10 includes a first generally planar magnetic field generating coil 60. The first generally planar magnetic field generating coil 60 has a first coil trace 14 wound in, for instance, a decreasing radial spiral, which passes about a first central portion 50. The first coil trace 14 has a first electric current 18 traveling in a first directional path 20 and has a first plurality of separated portions 22 each having a first respective set of different radii R(1–i) from the first central portion 50 along a bisecting line B. The first planar coil 60 has a second coil trace 24, has a second electric current 19 traveling along a second directional path 21 which is parallel to the first direction 20. The first planar coil 60 further has a second plurality of separated portions 26, each has a second respective set of different radii R(1–j) from the first central portion 50 along the bisecting line B. As shown in FIGS. 1, 2a-2c, the central portions can be along coil center line C and C'. The first and second coil traces 14 and 24 are interleaved so that along the bisecting line B-C, traces from the first coil are placed adjacent to the traces of the second coil.

The probe 10 further has a second generally planar magnetic field generating coil 61, and a third coil trace 32 wound in, for instance, a decreasing radial spiral which passes about a second central portion 51. The third coil trace 32 has a third electric current 38 traveling in a third direction 40 and has a third plurality of separated portions each having a third respective set of different radii from the second central portion 51 along a second bisecting line D in a similar manner to that described in reference to magnetic field generating coil 60 above. The second planar coil 61 has a fourth coil trace 44 and a fourth electric current 46 traveling in a fourth direction 28 that is parallel to the third direction 40. The fourth coil trace 44 has a fourth plurality of separated portions each having a fourth respective set of different radii from the second central portion 51 along the second bisecting line D in a similar manner to that described in reference to magnetic field generating coil 60 above. The third and fourth coils traces 32 and 44 are interleaved so that the along the bisecting line C'-D, traces from the third coil are placed adjacent to the traces of the fourth coil.

It is not necessary that the radii of the various coils constituting the magnetic stimulation probe 10 have decreasing spiral traces of constant uniform radius. As shown in FIG. 2b the radii can be non-uniform. The spiral traces may optionally be placed close to one another largely dependent on the operating voltage of the coils. Additionally, the spiral traces do not necessarily have to conform to a generally circular geometry as depicted in FIGS. 2a-2c. Alternate configurations are possible including generally square, rectangular or combinations of circular, square, rectangular or other geometries.

The first and second coils 60 and 61 can be interconnected in various ways known to those skilled in the art. FIGS. 2b and 2c depict several possible interconnection methods all designed to produce an intense, generally focused magnetic field. The first and second planar coils 60 and 61 when energized together produce a generally focused magnetic field due to the respective polarity of each coil. For example, in FIG. 3 the magnetic field lines optionally point down for coil 60 and would point up for coil 61. Optionally, the first trace 14 is electrically coupled to the third trace 32, thus linking the first current path with the third current path and the second trace 24 is electrically coupled to the fourth trace 44, thus linking the second current path with the fourth current path. While the first and second coils 60 and 61 can be disposed on the same plane, they may be angled with respect to each other as generally shown in FIG. 1. Further, first and second coils be overlapping as generally shown in FIG. 2a, thus placing a portion of the second coil over or under a portion of the first coil. In this regard, it is possible for the second coil to overlap the first coil to an arbitrary degree or not at all, as depicted in FIG. 2b. In single coil probes, the traces can be electrically coupled and driven together such that the second trace is electrically coupled to the first trace.

The first and second coils can be formed of roughly rectangular traces having a first flat surface, having a trace thickness, and which have a width generally perpendicular to the first and second coil centerlines C, C' as generally shown in FIG. 3 and more specifically in FIG. 1. Optionally, the first and second coils can be formed of substantially circular cross-section conductors as depicted generally in FIG. 2a. Additionally, the first and second coils can be formed on a flexible circuit, where the first and second coils can be formed of flexible rectangular traces having a first flat surface, having a trace thickness, and which have a width generally perpendicular to the first and second coil centerlines C,C'.

Figure 4:
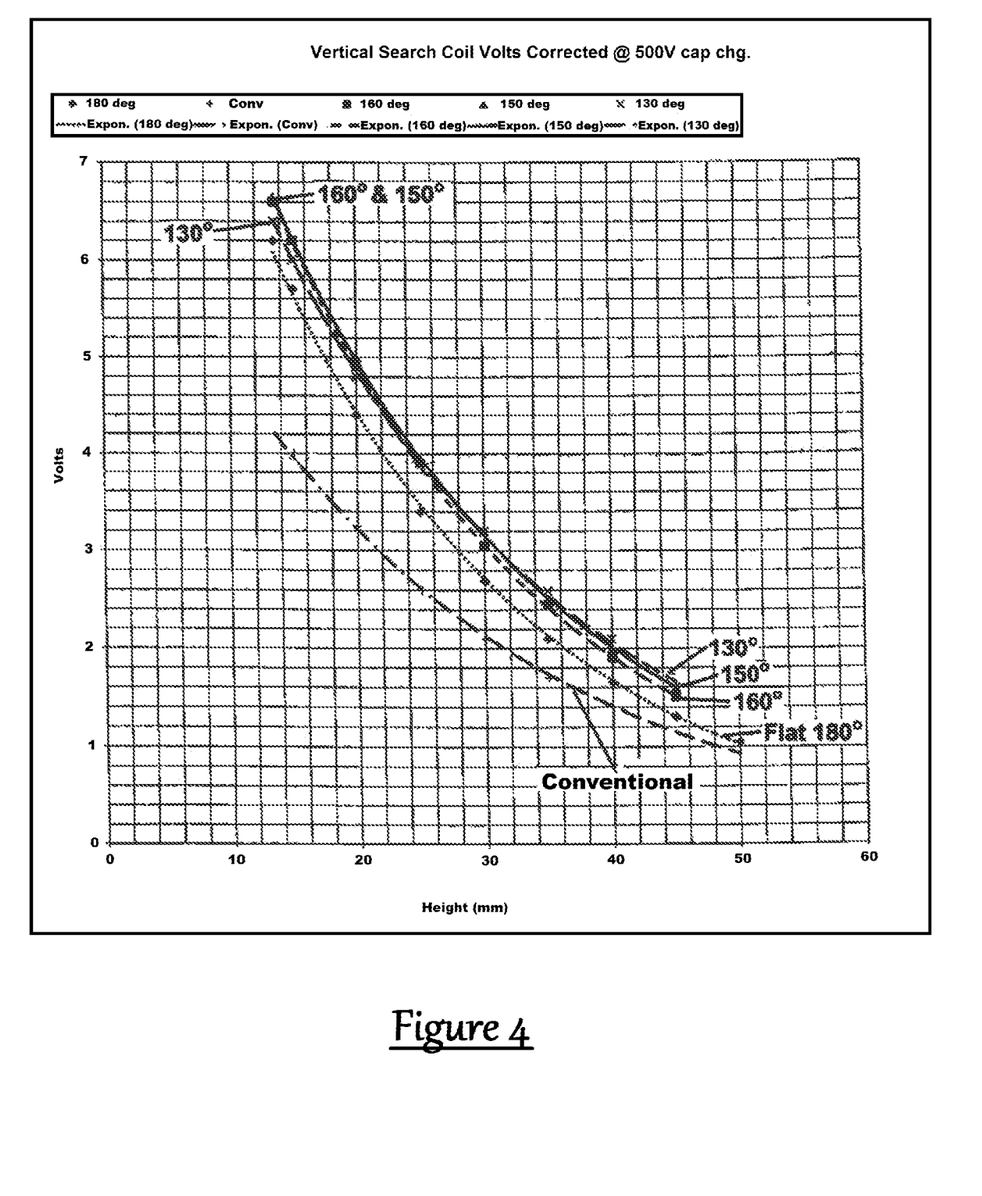
FIG. 4 represents a graph of the field intensity vs height above the probe for the magnetic stimulation probe shown in FIG. 1 compared to a standard magnetic stimulation probe of commercial design.

FIG. 4 represents the measured magnetic field output of the magnetic stimulation probe shown in FIG. 1 compared to a standard conventional two-coil planar magnetic stimulation probe of commercial design modeled on the Magstim MC-B70 stimulator coil using round Litz wire ("Conventional") which does not employ the interleaved winding technique of the present invention. The magnetic stimulation probe in FIG. 1 according to the present teaching employs the interleaved winding technique as described above. The measurement is performed using a small 5-turn flat spiral sensor coil as seen in FIG. 1 above the stimulator probe. The stimulator probe was driven by a current resulting from a fixed voltage across the driving capacitor of 500 volts. The measurements shown in FIG. 4 are the voltage across the spiral sensor coil of the first peak of the resulting pulsed waveform at various heights in mm between the center of the spiral sensor coil and the coil conductors above the center of the probe as a function of the bend angle between the 2 coils of the probe. The values shown assume an 8.5 cm radius spherical cranium and are corrected therefore.

Depicted in FIG. 4 are both the actual sensor output voltages as well as exponential curves fit to these data. The commercial design probe is labeled "Conventional" which is a flat planar probe and the remaining curves refer to a magnetic stimulation probe as shown in FIG. 1 which is constructed in such a manner as to allow the angle between the two coils therein to be changed from flat (180°) to 130°. It is clear that the curves for both magnetic stimulation probes are well-behaved and, for the bendable probe of the current teaching, generally increase in magnitude with decreasing bend angle from flat (180°) ie greater bend.

| Height (mm) | 180 deg (Vpk) | 160 deg (Vpk) | 150 deg (Vpk) | 130 deg (Vpk) | Conventional (Vpk) |
| --- | --- | --- | --- | --- | --- |
| 13.5 | 6.20 | 6.60 | 6.64 | 6.40 | |
| 15 | 5.70 | 6.20 | 6.20 | 6.00 | 4.00 |
| 20 | 4.40 | 4.90 | 5.00 | 4.80 | 3.25 |
| 25 | 3.40 | 3.90 | 3.95 | 3.90 | 2.60 |
| 30 | 2.70 | 3.05 | 3.20 | 3.20 | 2.10 |
| 35 | 2.10 | 2.45 | 2.50 | 2.60 | 1.70 |
| 40 | 1.65 | 1.90 | 2.00 | 2.10 | 1.40 |
| 45 | 1.30 | 1.50 | 1.60 | 1.60 | |
| 50 | 1.05 | | | | 0.95 |

This is to be expected as the focality and field projection increase as the coils are "bent" together to enhance the cooperation between the two magnetic fields. It is further seen that for all bend angles, the magnetic stimulation probe of the present teaching outperforms the probe of commercial design by a substantial margin. It is also evident that there is an optimal angle as the bend angle increases away from flatness with approximately 150° as optimal.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A magnetic stimulation probe operable to produce a probe electromagnetic field within a selected region of an anatomy of a patient comprising:
   a first generally planar magnetic field generating coil having a first coil trace having a decreasing radial spiral which passes about a first central portion, the first coil trace having a first electric current traveling along a first directional path and having a first plurality of separated portions each having a first respective set of different radii from the first central portion along a bisecting line, the first coil trace having a first end at a first outer surface and a second end at an inner surface of the coil, the first planar coil having a second coil trace having a second electric current traveling in a second directional path which is interleaved within the first coil trace of the first coil and parallel to the first directional path but in a direction opposite to the first directional path, and having a second plurality of separated portions each having a second respective set of different radii from the first central portion along the bisecting line, the second trace having a third end at the first outer surface and a fourth end at an inner surface of the coil;
   wherein the probe electromagnetic field is operable to induce a current in a conductive material, and wherein the first and third ends are electrically coupled; and
   an alignment member configured to allow placement of the probe adjacent a patient's body, wherein the magnetic stimulation probe is operable to stimulate a selected portion of the patient.

2. The system of claim 1, wherein the alignment member and the magnetic stimulation probe are formed as a single unit.

3. The system of claim 2 further comprising a second generally planar magnetic field generating coil having a third coil trace having a decreasing radial spiral which passes about a second central portion, the third coil trace having a third electric current traveling along a third directional path and having a third plurality of separated portions each having a third respective set of different radii from the second central portion along a second bisecting line, the second planar coil having a fourth coil trace interleaved between the third coil trace of the second coil and having a fourth electric current traveling along a fourth directional path which is parallel to the third directional path but a direction opposite to the third directional path, and having a fourth plurality of separated portions each having a fourth respective set of different radii from the second central portion along the bisecting line, the third and fourth coils traces being alternated and interleaved along the bisecting line.

4. The system of claim 3, wherein the first and second planar coils produce a focused high intensity magnetic field at a distance from the coils.

5. The system of claim 3, wherein the first trace is electrically coupled to the third trace.

6. The system of claim 3, wherein the second trace is electrically coupled to the fourth trace.

7. The system of claim 3, wherein the first trace is electrically connected to the second trace and the third trace is electrically connected to the fourth trace.

8. The system of claim 3, wherein a portion of the first generally planar coil is overlapping a portion of the second generally planar coil.

9. The system of claim 1, wherein the second trace is electrically coupled to the first trace.

10. A magnetic stimulation probe operable to produce a probe electromagnetic field within a selected region of an anatomy of a patient comprising:
 a first magnetic field generating coil having a first coil trace having a decreasing radial spiral which passes about a first central portion, the first coil trace having a first electric current traveling along a first directional path and having a first plurality of separated portions each having a first respective set of different radii from the first central portion along a bisecting line, the first coil having a second coil trace interleaved between the first coil trace of the first coil and having a second electric current traveling in a second directional path which is parallel to and opposite the first directional path, and having a second plurality of separated portions each having a second respective set of different radii from the first central portion along the bisecting line;
 wherein the probe electromagnetic field is operable to induce a current in a conductive material;
 an alignment member configured to allow placement of the probe adjacent a patient's body; and
 a second magnetic field generating coil having a third coil trace having a decreasing radial spiral which passes about a second central portion, the third coil trace having a third electric current traveling in a third directional path and having a third plurality of separated portions each having a third respective set of different radii from the second central portion along a second bisecting line, the second coil having a fourth coil trace interleaved between the third coil trace of the second coil and having a fourth electric current traveling in a fourth directional path which is parallel to and opposite the third directional path, and having a fourth plurality of separated portions each having a fourth respective set of different radii from the second central portion along the bisecting line.

11. The system of claim 10, wherein the first and second coils produce a focused high intensity magnetic field within a predefined volume at a predetermined distance from the coils.

12. The system of claim 10, wherein the first trace is electrically coupled to the third trace, and wherein the second trace is electrically coupled to the fourth trace.

13. The system of claim 10, wherein the first trace is electrically connected to the second trace and the third trace is electrically connected to the fourth trace.

14. The system of claim 10, wherein a portion of the first coil is disposed one of adjacent to and overlapping a portion of the second coil.

15. The system of claim 10, wherein the first and second coils are formed on a flexible circuit.

16. The system of claim 10, wherein the first and second magnetic field generating coils are bent together.

17. The system of claim 10, wherein the second trace is electrically coupled to the first trace.

18. A magnetic stimulation probe operable to produce a probe electromagnetic field within a selected region of an anatomy of a patient comprising:
 a first magnetic field generating coil having a first coil trace having a decreasing radial spiral which passes about a first central portion, the first coil trace having a first electric current traveling along a first directional path and having a first plurality of separated portions each having a first respective set of different radii from the first central portion along a bisecting line, the first coil having a second coil trace interleaved between first coil trace of the first coil and having a second electric current traveling in a second directional path which is parallel to and opposite the first directional path, and having a second plurality of separated portions each having a second respective set of different radii from the first central portion along the bisecting line;
 wherein the probe electromagnetic field is operable to induce a current in a conductive material;
 a second magnetic field generating coil having a third coil trace having a decreasing radial spiral which passes about a second central portion, the third coil trace having a third electric current traveling in a third directional path and having a third plurality of separated portions each having a third respective set of different radii from the second central portion along a second bisecting line, the second coil having a fourth coil trace interleaved between the third coil trace of the second coil and having a fourth electric current traveling in a fourth directional path which is parallel to and opposite the third directional path, and having a fourth plurality of separated portions each having a fourth respective set of different radii from the second central portion along the bisecting line, wherein the first trace is electrically coupled to the third trace, and wherein the second trace is electrically coupled to the fourth trace and wherein the first and second coils produce a focused high intensity magnetic field within a predefined volume at a predetermined distance from the first and second coils.

19. The system of claim 18, wherein a portion of the first coil is disposed one of adjacent to and overlapping a portion of the second coil.

20. The system of claim 18, wherein the first and second coils are formed on a flexible circuit.

* * * * *